United States Patent
Lee et al.

(10) Patent No.: US 9,788,737 B2
(45) Date of Patent: Oct. 17, 2017

(54) VITAL SIGNS MEASUREMENT SYSTEM, DETECTING METHOD OF THE VITAL SIGNS MEASUREMENT SYSTEM, AND VITAL SIGNS MEASUREMENT EARPHONE

(71) Applicant: Cheng Uei Precision Industry Co., Ltd., New Taipei (TW)

(72) Inventors: Cheng Lee, New Taipei (TW); Kuo Yang Wu, New Taipei (TW); Wen-Bing Hsu, New Taipei (TW); Hsiang-Ling Chung, New Taipei (TW)

(73) Assignee: CHENG UEI PRECISION INDUSTRY CO., LTD., New Taipei (TW)

( * ) Notice: Subject to any disclaimer, the term of this patent is extended or adjusted under 35 U.S.C. 154(b) by 358 days.

(21) Appl. No.: 14/594,127

(22) Filed: Jan. 10, 2015

(65) Prior Publication Data

US 2016/0198964 A1    Jul. 14, 2016

(51) Int. Cl.
*A61B 5/02* (2006.01)
*A61B 5/024* (2006.01)
*A61B 5/00* (2006.01)

(52) U.S. Cl.
CPC ...... *A61B 5/02427* (2013.01); *A61B 5/02438* (2013.01); *A61B 5/6815* (2013.01); *A61B 5/6898* (2013.01); *A61B 5/721* (2013.01); *A61B 5/725* (2013.01); *A61B 5/7246* (2013.01); *A61B 5/7257* (2013.01); *A61B 5/7214* (2013.01)

(58) Field of Classification Search
CPC ............ A61B 5/02427; A61B 5/02438; A61B 5/02444; A61B 5/6815; A61B 5/6816; A61B 5/6817; A61B 5/6898; A61B 5/721; A61B 5/7246; A61B 5/725; A61B 5/7257; A61B 5/7214
See application file for complete search history.

*Primary Examiner* — Mallika D Fairchild
(74) *Attorney, Agent, or Firm* — Cheng-Ju Chiang

(57) ABSTRACT

A vital signs measurement system includes a plurality of light sources emitting into a subject's skin. A plurality of photo sensors receives lights reflected from the subject's skin and converts the lights to a plurality of signals. A processing module receives the plurality of signals and transforms the plurality of signals to a PPG signal by analyzing a correlation coefficient between every two ones of the plurality of signals. The vital signs measurement system improves the measurement accuracy of the physiological information of the participant by the correlation coefficient.

9 Claims, 6 Drawing Sheets

VITAL SIGNS MEASUREMENT SYSTEM, DETECTING METHOD OF THE VITAL SIGNS MEASUREMENT SYSTEM, AND VITAL SIGNS MEASUREMENT EARPHONE

BACKGROUND OF THE INVENTION

1. Field of the Invention

Embodiments of the present disclosure relate to the field of vital signs measurement, and more particularly to a system, detecting method, and vital signs measurement earphone for improving the accuracy of the vital signs measurement.

2. The Related Art

A traditional physiological function detecting earphone for detecting the heart rate variability (HRV) includes an earphone body, a light source and a light sensor. The earphone body has an earplug made of pervious to light material. In use, the earplug of the earphone body is inserted into the ear canal of a participant, then light emitted by the light source penetrates through the earplug and is reflected by the wall of the ear canal, and last the light sensor senses the reflected light of changes in a period of time to get Photoplethysmography (PPG) signals so as to detect the HRV.

However, manufacturing material of the earplug has an effect on transmittance of light through the earplug. Furthermore, the earphone is apt to move in the ear canal along with the shaking of the participant, so that will easily cause an interspace between the earplug and the wall of the ear canal. As a result, the light outside the ear canal can go into the ear canal through the interspace so that will affect the PPG signals got by the light sensor and ultimately affect the accuracy of the HRV.

Therefore, a vital signs measurement system, method, and earphone capable of overcoming the abovementioned problems are required.

SUMMARY OF THE INVENTION

An object of the present invention is to provide a vital signs measurement system which includes a plurality of light sources emitting into a subject's skin. A plurality of photo sensors receives lights reflected from the subject's skin and converts the lights to a plurality of signals. A processing module receives the plurality of signals and transforms the plurality of signals to a PPG (Photoplethysmography) signal by analyzing a correlation coefficient between every two ones of the plurality of signals. The correlation coefficient is calculated as follows:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

Where $R_{xy}$ is the correlation coefficient between the every two ones of the plurality of signals, x and y are two signal values corresponding to the every two ones of the plurality of signals respectively. Wherein if each the correlation coefficient is within an allowable value, then sum all of the plurality of signals to obtain the PPG signal; if not, use the following formula to get a correlation signal between the every two ones of the plurality of signals. The correlation signal is expressed in $S_{xy}$:

$$S_{xy} = (1 - R_{xy})(x+y)$$

then sum all of the correlation signal $S_{xy}$ to obtain the PPG signal.

Another object of the present invention is to provide a detecting method of the vital signs measurement. The detecting method includes the steps. Receive a plurality of signals which are converted from reflected lights by a subject's skin, and then process the plurality of signals by high pass filtering, low pass filtering, DC filtering, downsampling and normalizing the amplitude of the plurality of signals. Calculate a correlation coefficient between every two ones of the plurality of signals according to the following formula:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

where $R_{xy}$ is the correlation coefficient between the every two ones of the plurality of signals, x and y are two signal values corresponding to the every two ones of the plurality of signals respectively. Analyze the correlation coefficient to transform the plurality of signals to a PPG (Photoplethysmography) signal, wherein if each the correlation coefficient is within an allowable value, then sum all of the plurality of signals to obtain the PPG signal; if not, use the following formula to get a correlation signal between the every two ones of the plurality of signals, the correlation signal is expressed in $S_{xy}$:

$$S_{xy} = (1 - R_{xy})(x+y)$$

then sum all of the correlation signal $S_{xy}$ to obtain the PPG signal.

Another object of the present invention is to provide a vital signs measurement earphone. The vital signs measurement earphone includes an earphone body equipped with a processing module therein. An insert element is located at one side of the earphone body. A light-permeable earplug is mounted at the free end of the insert element. A plurality of light sources is disposed at the periphery of the insert element. Lights from the plurality of light sources penetrate through the light-permeable earplug at different angles along radial directions of the insert element respectively onto a subject's ear canal wall. A plurality of photo sensors is disposed at the periphery of the insert element. The photo sensors receive reflected lights by the subject's ear canal wall and then convert the reflected lights to a plurality of signals. The processing module receives the plurality of signals and transforms the plurality of signals to a PPG (Photoplethysmography) signal by analyzing a correlation coefficient between every two ones of the plurality of signals. The correlation coefficient is calculated as follows:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

where $R_{xy}$ is the correlation coefficient between the every two ones of the plurality of signals, x and y are two signal values corresponding to the every two ones of the plurality of signals respectively. If each the correlation coefficient is within an allowable value, then sum all of the plurality of signals to obtain the PPG signal. If not, use the following formula to get a correlation signal between the every two ones of the plurality of signals. The correlation signal is expressed in $S_{xy}$:

$$S_{xy} = (1 - R_{xy})(x+y)$$

then sum all of the correlation signal $S_{xy}$ to obtain the PPG signal.

As described above, the vital signs measurement system, the detecting method of the vital signs measurement system, and the vital signs measurement earphone can effectively improve the measurement accuracy of the physiological information of the participant by the correlation coefficient.

BRIEF DESCRIPTION OF THE DRAWINGS

The present invention will be apparent to those skilled in the art by reading the following description thereof, with reference to the attached drawings, in which.

DETAILED DESCRIPTION OF THE EMBODIMENT

Figure 1:
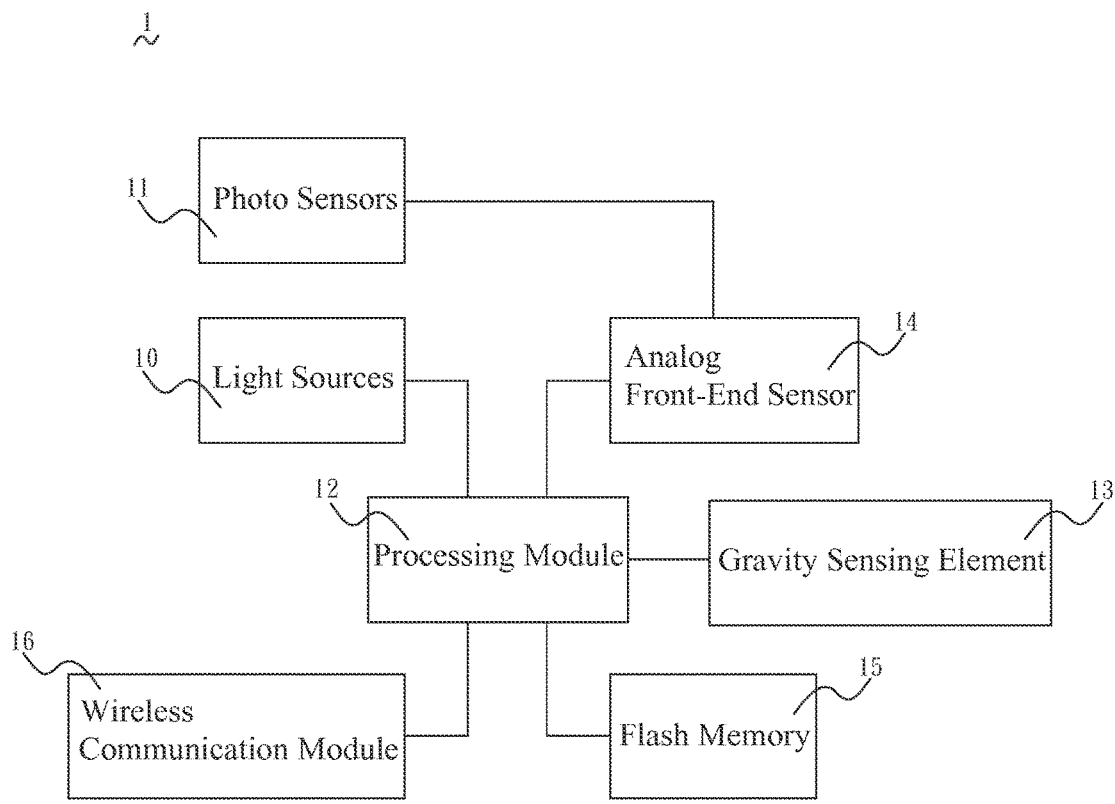
FIG. 1 is a block diagram of a vital signs measurement system according to an embodiment of the present invention.
Figure 2:
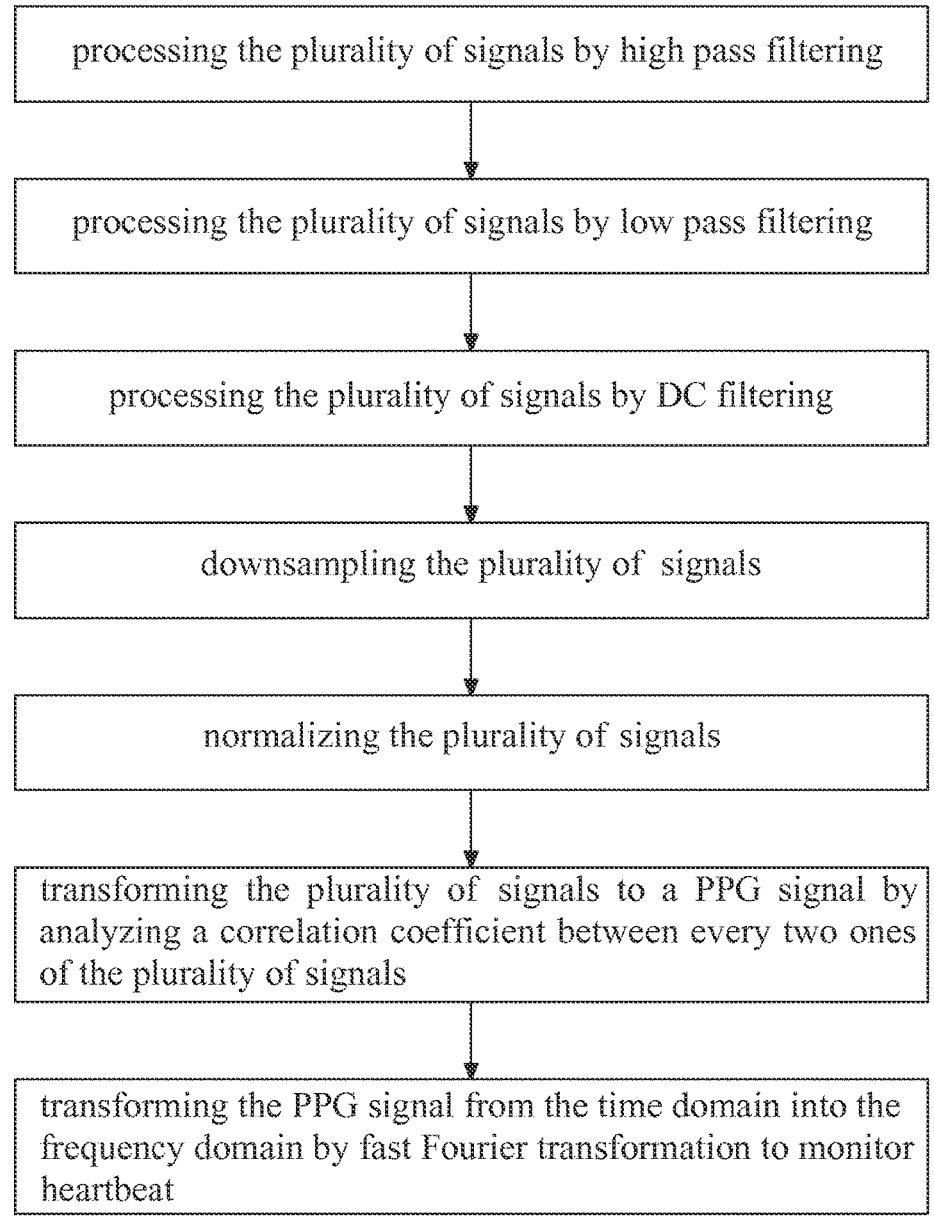
FIG. 2 is a flow diagram showing a processing module of the vital signs measurement system processes a plurality of signals which is converted from reflected lights by a subject's skin.
Figure 3:
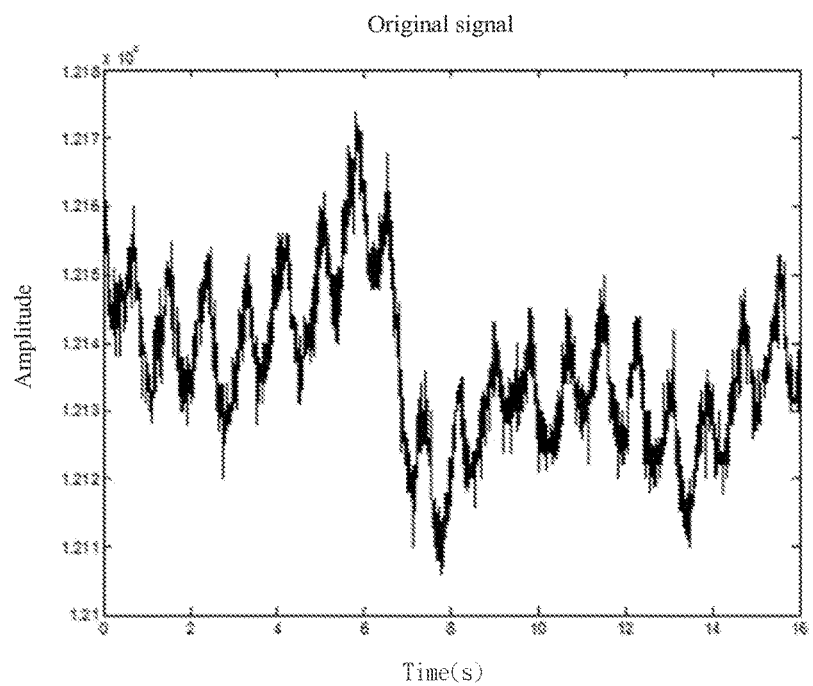
FIG. 3 is a wave diagram of an original signal of the present invention.
Figure 4:
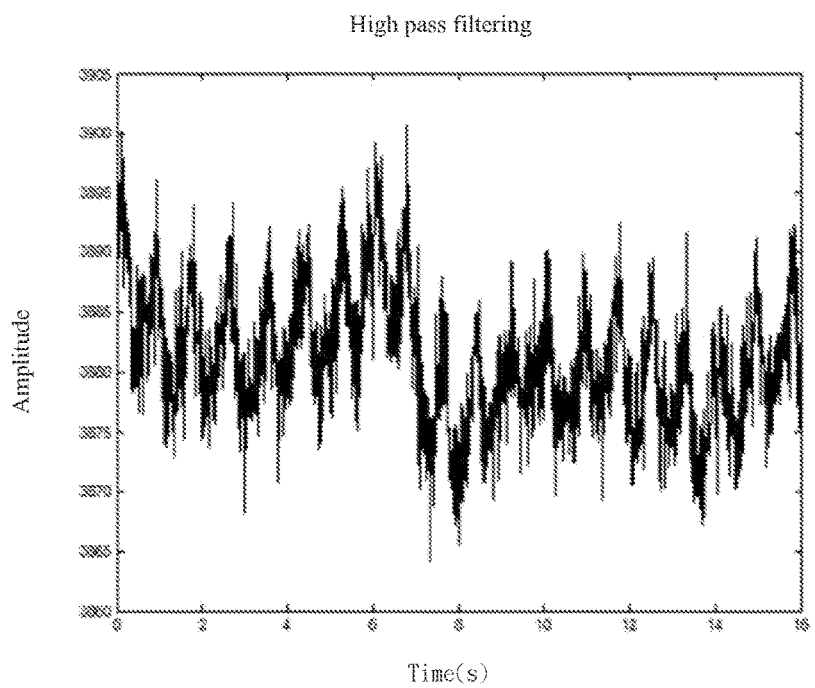
FIG. 4, FIG. 5 and FIG. 6 are three wave diagrams showing the original signal of FIG. 3 is successively processed by a high pass filtering, a low pass filtering and a DC filtering.
Figure 5:
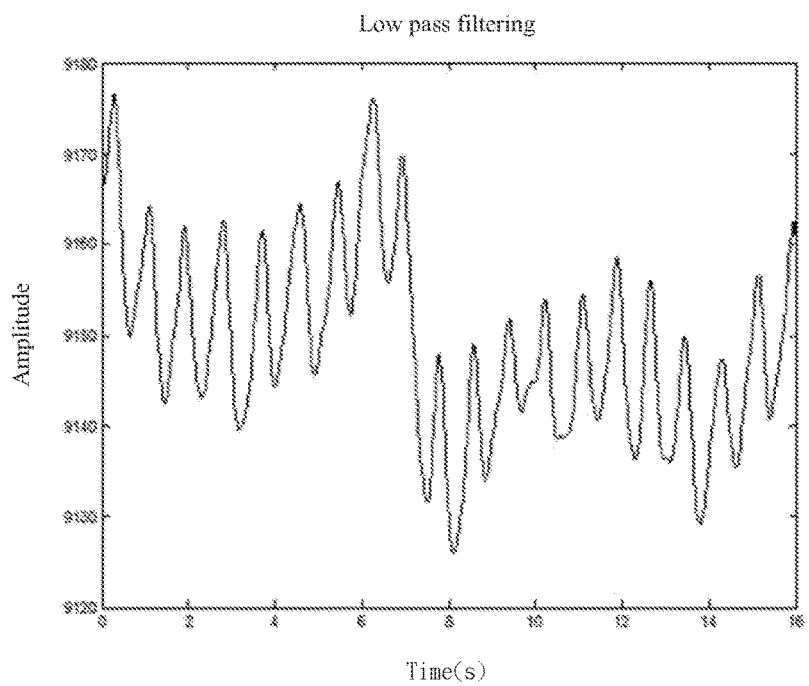
Figure 6:
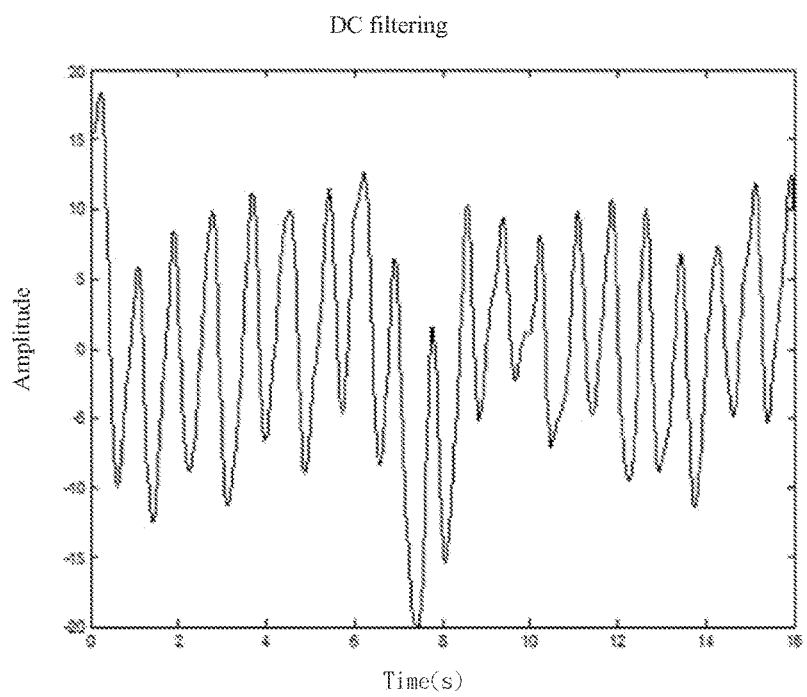

Referring to FIG. 1, a vital signs measurement system 1 according to an embodiment of the present invention includes a plurality of light sources 10, a plurality of photo sensors 11, and a processing module 12.

The light sources 10 emit into a subject's skin. The photo sensors 11 receive lights reflected from the subject's skin and convert the lights to a plurality of signals. The processing module 12 receives the plurality of signals and transforms the plurality of signals to a heart rate.

Referring to FIG. 2 to FIG. 6, because the light sources 10 emit into different parts of the subject's skin, the lights reflected by the different parts of the subject's skin have different values, and accordingly, the plurality of signals converted from the photo sensors 11 have different values. Furthermore, each of the photo sensors 11 is affected by light noise. Therefore, a difference is between each every two values of the plurality of signals. The difference can be analyzed by a correlation coefficient between every two ones of the plurality of signals calculated by the processing module 12.

In detail, the processing module 12 receives the plurality of signals and processes the plurality of signals in noise elimination. The noise elimination is achieved by high pass filtering, low pass filtering, DC filtering, downsampling and normalizing the amplitude of the plurality of signals, so that the amplitude of the plurality of signals would be utilized to analyze the correlation coefficient. The processing module 12 obtains a PPG (Photoplethysmography) signal through the correlation coefficient. The PPG signal is transformed from the time domain into the frequency domain by fast Fourier transformation to monitor heartbeat.

The correlation coefficient between the every two ones of the plurality of signals is calculated as follows:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

where $R_{xy}$ is the correlation coefficient between the every two ones of the plurality of signals, x and y are two signal values corresponding to the every two ones of the plurality of signals respectively. Wherein, if each the correlation coefficient is within an allowable value, then sum all of the plurality of signals to obtain the PPG signal; if not, use the following formula to get a correlation signal between the every two ones of the plurality of signals. The correlation signal is expressed in $S_{xy}$:

$$S_{xy}=(1-R_{xy})(x+y)$$

Then sum all of the correlation signal $S_{xy}$ to obtain the PPG signal.

Referring to FIG. 1, the vital signs measurement system 1 further includes a gravity sensing element 13 which is configured to sense a vibration and then converts the vibration to a motion signal. The processing module 12 compares the amplitude of the PPG signal with the one of the motion signal to serve to produce precise the PPG signal in reducing motion artifact.

In the embodiment of the present invention, the photo sensors 11 transmit the plurality of signals into the processing module 12 through an analog front-end sensor 14.

The vital signs measurement system 1 further includes a flash memory 15 and a wireless communication module 16. The flash memory 15 is configured to store heartbeat information from the processing module 12. The wireless communication module 16 is configured to perform communication between the processing module 12 and other electronic devices.

In the embodiment of the present invention, the photo sensors 11 are arranged in three into a ring at approximately 120° between each two adjacent ones. In detail, the photo sensors 11 include a first photo sensor, a second photo sensor and a third photo sensor which convert the lights to a first signal S1, a second signal S2 and a third signal S3 respectively. The processing module 12 processes the first signal S1, the second signal S2 and the third signal S3 in the noise elimination, then uses $R_{xy}$ formula to get three correlation coefficients R12, R23 and R31, wherein R12 is the correlation coefficient of the first signal S1 and the second signal S2, R23 is the correlation coefficient of the second signal S2 and the third signal S3, and R31 is the correlation coefficient of the third signal S3 and the first signal S1. If all of the three correlation coefficients are within the allowable value, for example, if the allowable value is 0.4 and all of the three correlation coefficients are greater than or equal to 0.4, use the following formula to obtain the PPG signal:

PPG signal=S1+S2+S3

If any one of the correlation coefficients is less than 0.4, use the following formula to obtain the PPG signal:

PPG signal=(1−R12)(S1+S2)+(1−R23)(S2+S3)+(1−R31)(S1+S3)

Then the PPG signal is transformed from the time domain into the frequency domain by fast Fourier transformation to monitor heartbeat.

Figure 7:
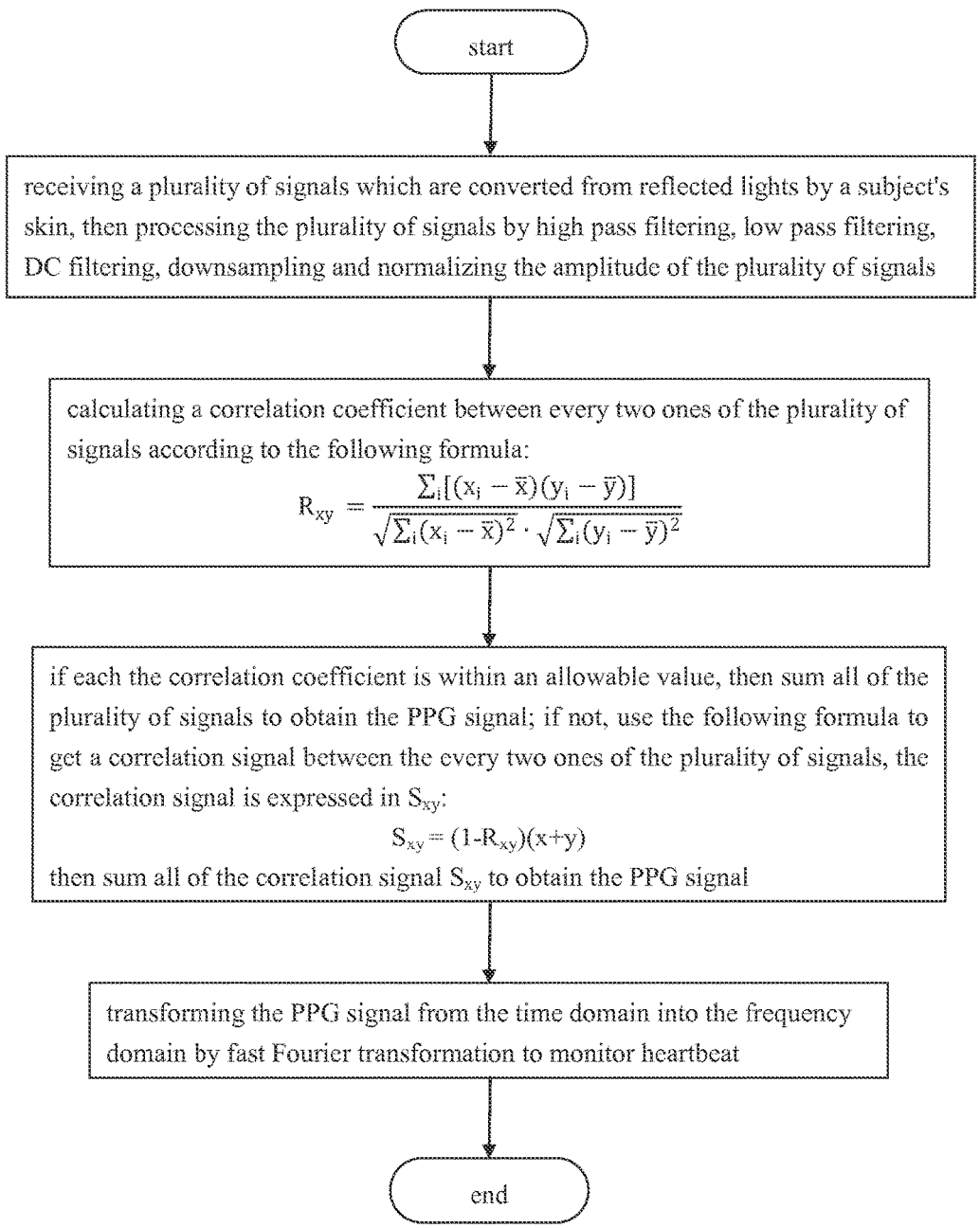
FIG. 7 is a flow diagram showing a detecting method of the vital signs measurement system.

Referring to FIG. 7, a detecting method of the vital signs measurement system 1 includes the following steps.

Step 1: receive a plurality of signals which are converted from reflected lights by a subject's skin, then process the plurality of signals by high pass filtering, low pass filtering, DC filtering, downsampling and normalizing the amplitude of the plurality of signals.

Step 2: calculate a correlation coefficient between every two ones of the plurality of signals according to the following formula:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

where $R_{xy}$ is the correlation coefficient between the every two ones of the plurality of signals, x and y are two signal values corresponding to the every two ones of the plurality of signals respectively.

Step 3: analyze the correlation coefficient to transform the plurality of signals to a PPG (Photoplethysmography) signal, wherein if each the correlation coefficient is within an allowable value, then sum all of the plurality of signals to obtain the PPG signal; if not, use the following formula to get a correlation signal between the every two ones of the plurality of signals, the correlation signal is expressed in $S_{xy}$:

$$S_{xy}=(1-R_{xy})(x+y)$$

then sum all of the correlation signal $S_{xy}$ to obtain the PPG signal.

Step 4: transform the PPG signal from the time domain into the frequency domain by fast Fourier transformation to monitor heartbeat.

Figure 8:
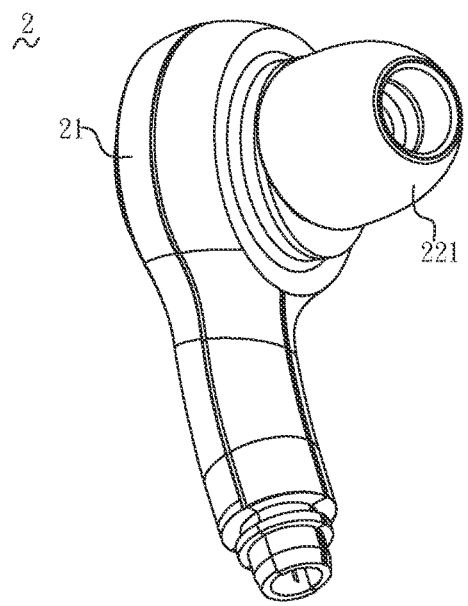
FIG. 8 is a perspective view of a vital signs measurement earphone according to an embodiment of the present invention.
Figure 9:
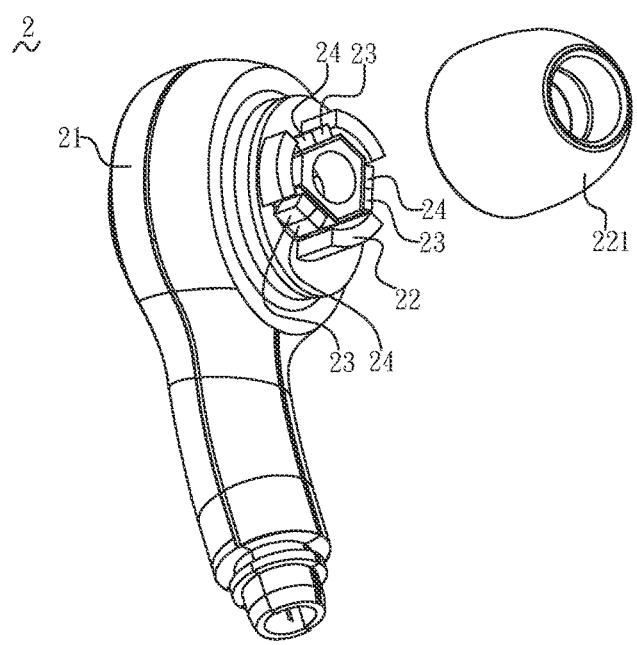
FIG. 9 is a partly exploded view of the vital signs measurement earphone of FIG. 8.

Referring to FIG. 8 to FIG. 9, a vital signs measurement earphone 2 includes an earphone body 21 equipped with the processing module 12 therein, an insert element 22, a light-permeable earplug 221, a plurality of light sources 23, and a plurality of photo sensors 24. The insert element 22 is located at one side of the earphone body 21 for being positioned in a subject's ear canal. The light-permeable earplug 221 is mounted at the free end of the insert element 22. The plurality of light sources 23 is disposed at the periphery of the insert element 22. Lights from the plurality of light sources 23 penetrate through the light-permeable earplug 221 at different angles along radial directions of the insert element 22 respectively onto a subject's ear canal wall. The photo sensors 24 are disposed at the periphery of the insert element 22. The photo sensors 24 receive the reflected lights by the subject's ear canal wall and then convert the reflected lights to a plurality of signals. The processing module 12 receives the plurality of signals and processes the plurality of signals by high pass filtering, low pass filtering, DC filtering, downsampling and normalizing the amplitude of the plurality of signals. The processing module 12 further transforms the plurality of signals to a PPG signal by analyzing a correlation coefficient between every two ones of the plurality of signals.

Preferably, the photo sensors 24 are evenly distributed on the radial direction of the periphery of the insert element 22.

When the vital signs measurement earphone 2 sways up and down, the photo sensors 24 on the top and the photo sensors 24 on the bottom obtain different values of signals, because different gap distances are between each of the photo sensors 24 and the subject's ear canal wall. If the photo sensor 24 is close to the subject's ear canal wall, the light noise is smaller. If the photo sensor 24 is spaced apart from the subject's ear canal wall, the light noise is bigger. Therefore, the influence of the light noise on the plurality of signals is embodied in the correlation coefficient.

As described above, the vital signs measurement system 1, the detecting method of the vital signs measurement system 1, and the vital signs measurement earphone 2 can effectively improve the measurement accuracy of the physiological information of the participant by the correlation coefficient, and furthermore, can accurately measure the physiological information during exercise.

What is claimed is:

1. A vital signs measurement system to monitor heartbeat of a subject, comprising:
   a plurality of light sources adapted to emit light into a subject's skin;
   a plurality of photo sensors adapted to receive light reflected from the subject's skin and converting the received light to a plurality of signals;
   a processing module receiving the plurality of signals and transforming the plurality of signals to a PPG (Photoplethysmography) signal by calculating a correlation coefficient between every two ones of the plurality of signals, the correlation coefficient being calculated as follows:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

where $R_{xy}$ is the correlation coefficient between the every two ones of the plurality of signals, x and y are two signal values corresponding to the every two ones of the plurality of signals respectively;
   wherein if the correlation coefficient is within an allowable value, then sum all of the plurality of signals to obtain the PPG signal; if not, use a following formula to get a correlation signal between the every two ones of the plurality of signals, the correlation signal is expressed in $S_{xy}$:

$$S=(1-R_{xy})(x+y)$$

then sum all of the correlation signal $S_{xy}$ to obtain the PPG signal to monitor heartbeat of the subject.

2. The vital signs measurement system as claimed in claim 1, wherein the PPG signal is transformed from a time domain into a frequency domain by fast Fourier transformation to monitor heartbeat.

3. The vital signs measurement system as claimed in claim 1, wherein the plurality of photo sensors includes a first photo sensor, a second photo sensor and a third photo sensor which convert the light reflected from the subject's skin to a first signal S1, a second signal S2 and a third signal S3 respectively, the processing module processes the first signal S1, the second signal S2 and the third signal S3 to eliminate noise, then use the correlation coefficient (Rxy) formula to get three correlation coefficients R12, R23 and R31, if all of the three correlation coefficients are within the allowable value, use the following formula to obtain the PPG signal:

PPG signal=S1+S2+S3 if not, use the following formula to obtain the PPG signal:

PPG signal=(1−R12)(S1+S2)+(1−R23)(S2+S3)+(1−R31)(S1+S3)

then the PPG signal is transformed from a time domain into a frequency domain by fast Fourier transformation to monitor heartbeat.

4. The vital signs measurement system as claimed in claim 3, further comprising a gravity sensing element which is configured to sense a vibration and then convert the vibration to a motion signal, the processing module compares an amplitude of the PPG signal with an amplitude of the motion signal.

5. The vital signs measurement system as claimed in claim 1, wherein the photo sensors transmit the plurality of signals into the processing module through an analog front-end sensor.

6. The vital signs measurement system as claimed in claim 1, further comprising a flash memory and a wireless communication module, the flash memory is configured to store heartbeat information from the processing module, the wireless communication module is configured to perform communication between the processing module and other electronic devices.

7. A vital signs measurement earphone, comprising:
an earphone body equipped with a processing module therein;
an insert element located at one side of the earphone body;
a light-permeable earplug mounted at a free end of the insert element;
a plurality of light sources disposed at a periphery of the insert element, lights from the plurality of light sources penetrating through the light-permeable earplug at different angles along radial directions of the insert element respectively onto a subject's ear canal wall; and
a plurality of photo sensors disposed at the periphery of the insert element, the photo sensors adapted to receive lights reflected by the subject's ear canal wall and then converting the reflected lights to a plurality of signals;

wherein the processing module receives the plurality of signals and transforms the plurality of signals to a PPG (Photoplethysmography) signal by calculating a correlation coefficient between every two ones of the plurality of signals, the correlation coefficient is calculated as follows:

$$R_{xy} = \frac{\Sigma_i[(x_i - \bar{x})(y_i - \bar{y})]}{\sqrt{\Sigma_i(x_i - \bar{x})^2} \cdot \sqrt{\Sigma_i(y_i - \bar{y})^2}}$$

where Rxy is the correlation coefficient between the every two ones of the plurality of signals, x and y are two signal values corresponding to the every two ones of the plurality of signals respectively, if the correlation coefficient is within an allowable value, then sum all of the plurality of signals to obtain the PPG signal; if not, use a following formula to get a correlation signal between the every two ones of the plurality of signals, the correlation signal is expressed in Sxy:

$$S_{xy} = (1 - R_{xy})(x+y)$$

then sum all of the correlation signal Sxy to obtain the PPG signal to monitor heartbeat of the subject.

8. The vital signs measurement earphone as claimed in claim 7, further comprising a gravity sensing element which is configured to sense a vibration and then convert the vibration to a motion signal, the processing module compares an amplitude of the PPG signal with an amplitude of the motion signal.

9. The vital signs measurement earphone as claimed in claim 7, wherein the photo sensors are arranged at 120° between each two adjacent ones.

* * * * *